(12) United States Patent
Ghosh

(10) Patent No.: US 9,603,651 B2
(45) Date of Patent: Mar. 28, 2017

(54) METHODS FOR SIMULTANEOUS CARDIAC SUBSTRATE MAPPING USING SPATIAL CORRELATION MAPS BETWEEN NEIGHBORING UNIPOLAR ELECTROGRAMS

(71) Applicant: Medtronic, Inc., Minneapolis, MN (US)

(72) Inventor: Subham Ghosh, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 1 day.

(21) Appl. No.: 14/694,292

(22) Filed: Apr. 23, 2015

(65) Prior Publication Data

US 2015/0223863 A1    Aug. 13, 2015

Related U.S. Application Data

(62) Division of application No. 13/773,162, filed on Feb. 21, 2013, now Pat. No. 9,031,642.

(51) Int. Cl.
| | |
|---|---|
| *A61B 5/04* | (2006.01) |
| *A61B 18/12* | (2006.01) |
| *A61B 5/042* | (2006.01) |
| *A61B 5/0432* | (2006.01) |
| *A61B 5/044* | (2006.01) |

(Continued)

(52) U.S. Cl.
CPC .............. *A61B 18/12* (2013.01); *A61B 5/044* (2013.01); *A61B 5/046* (2013.01); *A61B 5/04012* (2013.01); *A61B 5/0422* (2013.01); *A61B 5/0432* (2013.01); *A61B 5/0452* (2013.01); *A61B 5/7246* (2013.01); *A61B 18/1492* (2013.01); *A61B 2018/00214* (2013.01); *A61B 2018/00267* (2013.01);
(Continued)

(58) Field of Classification Search
None
See application file for complete search history.

(56) References Cited

U.S. PATENT DOCUMENTS 5,676,153 A    10/1997    Smith et al.

FOREIGN PATENT DOCUMENTS

| EP | 0911059 A2 | 4/1999 |
|---|---|---|
| EP | 1178855 B1 | 8/2006 |

(Continued)

OTHER PUBLICATIONS

Konings et al., Configuration of Unipolar Atrial Electrograms During Electrically Induced Atrial Fibrillation in Humans, Circulation. 1997; 95: 1231-1241.

(Continued)

*Primary Examiner* — Eric D. Bertram
*Assistant Examiner* — Elizabeth K So
(74) *Attorney, Agent, or Firm* — Christopher & Weisberg, P.A.

(57) ABSTRACT

A base cardiac electrogram signal at a base electrode is recorded for a predetermined amount of time. A plurality of cardiac electrogram signals at a plurality of electrodes other than the base electrode are recorded for the predetermined amount of time. The base cardiac electrogram signal is compared with each of the plurality of cardiac electrogram signals. The similarities between the base cardiac electrogram signal and each of the plurality of cardiac electrogram signals is determined. A specific area of cardiac tissue where the base electrode is positioned is mapped based at least in part on the determined similarities.

15 Claims, 8 Drawing Sheets

(51) Int. Cl.
*A61B 5/046* (2006.01)
*A61B 5/00* (2006.01)
*A61B 5/0452* (2006.01)
*A61B 18/14* (2006.01)
*A61N 1/05* (2006.01)
*A61B 18/00* (2006.01)

(52) U.S. Cl.
CPC ............... *A61B 2018/00577* (2013.01); *A61B 2018/00839* (2013.01); *A61N 1/05* (2013.01)

(56) References Cited

FOREIGN PATENT DOCUMENTS

| | | |
|---|---|---|
| EP | 1760661 A2 | 3/2007 |
| WO | 0045700 A1 | 8/2000 |

OTHER PUBLICATIONS

Gaita et al., Different Patterns of Atrial Activationin Idiopathic Atrial Fibrillation: Simultaneous Multisite Atrial Mapping in Patients With Paroxysmal and Chronic Atrial Fibrillation, Journal of the American College of Cardiology, vol. 37, No. 2, 2001, pp. 1-8.

Punske et al., Spatial Methods of Epicardial Activation Time Determination in Normal Hearts, Annals of Biomedical Engineering, vol. 31, pp. 781-792, 2003.

Ravelli et al., Wave Similarity Mapping Shows the Spatiotemporal Distribution of FibrillatoryWave Complexity in the Human Right Atrium During Paroxysmal and Chronic Atrial Fibrillation, J Cardiovasc Electrophysiol, vol. 16, pp. 1071-1076, Oct. 2005.

Narayan et al., Computational Mapping Identifies Localized Mechanisms for Ablation of Atrial Fibrillation, PLOS ONE, Sep. 2012 | vol. 7 | Issue 9, pp. 1-8.

Lalani et al., Atrial Conduction Slows Immediately Before the Onset of Human Atrial Fibrillation, Journal of the American College of Cardiology, vol. 59, No. 6, 2012, Feb. 7, 2012:595-606.

Lahn Fendelander, MS, et al., Spatial Coherence, A New Method of Quantifying Myocardial Electrical Organization Using Multichannel Epicardial Electrograms, Journal of Electrocardiology vol. 30 No. 1, pp. 9-19, Jan. 1997.

Stephane Masse et al., Wave similarity of human ventricular fibrillation from bipolar electrograms, The European Society of Cardiology, pp. 10-19, 2007.

Flavia Ravelli, Ph.D. et al., Wave Similarity Mapping Shows the Spatiotemporal Distribution of Fibrillatory Wave Complexity in the Human Right Atrium During Paroxysmal and Chronic Atrial Fibrillation, Journal of Cardiovascular Electrophysiol, vol. 16, No. 10, pp. 1071-1076, Oct. 2005.

Guy Salama, Ph.D. et al., Imaging ventricular fibrillation, Journal of Electrocardiology 40, (2007) pp. S56-S61.

International Search Report and Written Opinion dated Apr. 29, 2014 for International Application Serial No. PCT/US2014/011012, International Filing Date: Jan. 10, 2014 consisting of 13 pages.

METHODS FOR SIMULTANEOUS CARDIAC SUBSTRATE MAPPING USING SPATIAL CORRELATION MAPS BETWEEN NEIGHBORING UNIPOLAR ELECTROGRAMS

CROSS-REFERENCE TO RELATED APPLICATION

This application is a divisional of patent application Ser. No. 13/773,162 (now U.S. Pat. No. 9,031,642), filed Feb. 21, 2013, entitled METHODS FOR SIMULTANEOUS CARDIAC SUBSTRATE MAPPING USING SPATIAL CORRELATION MAPS BETWEEN NEIGHBORING UNIPOLAR ELECTROGRAMS, the entirety of which is incorporated herein by reference.

STATEMENT REGARDING FEDERALLY SPONSORED RESEARCH OR DEVELOPMENT n/a

FIELD OF THE INVENTION

The present invention relates to a method and system for mapping cardiac substrate.

BACKGROUND OF THE INVENTION

A cardiac arrhythmia is a condition in which the heart's normal rhythm is disrupted. There are many types of cardiac arrhythmias, including supraventricular arrhythmias that begin above the ventricles (such as premature atrial contractions (PACs), atrial flutter, accessory pathway tachycardias, atrial fibrillation, and Atrioventricular nodal reentrant tachycardia (AVNRT)), ventricular arrhythmias that begin in the lower chambers of the heart (such as premature ventricular contractions (PVCs), ventricular tachycardia (VT), ventricular fibrillation, and long QT syndrome), and bradyarrhythmias that involve slow heart rhythms and may arise from disease in the heart's conduction system. Further, cardiac arrhythmias may be classified as reentrant or non-reentrant arrhythmias. In reentrant arrhythmias, the propagating wave of bioelectricity that normally spreads systematically throughout the four chambers of the heart instead circulates along a myocardial pathway and around an obstacle (reentry point) or circulates freely in the tissue as a scroll wave or spiral (referred to herein as "rotors"). In non-reentrant arrhythmias, propagation of the normal bioelectricity wave may be blocked or initiated at abnormal (ectopic) locations.

Certain types of cardiac arrhythmias, including ventricular tachycardia and atrial fibrillation, may be treated by ablation (for example, radiofrequency (RF) ablation, cryoablation, ultrasound ablation, laser ablation, and the like), either endocardially or epicardially. However, a physician must first locate the point of reentry, ectopic focus, or regions of abnormal conduction to effectively treat the arrhythmia. Unfortunately, locating the best site for ablation has proven to be very difficult, even for the most skilled physicians.

Cardiac electrical mapping (mapping the electrical activity of the heart that is associated with depolarization and/or repolarization of the myocardial tissues) is frequently used to locate an optimal site for ablation, for instance, a reentry point, ectopic focus, or a site of abnormal myocardium. However, the source of an arrhythmia may be difficult to determine based upon the sensed electrogram morphology. In addition to signals emanating from the local myocardium, the electrogram morphology may include fractionation due to poor electrode contact, electrode design, or complex electrical activity in the vicinity of the electrodes. The signals may also include "far-field" content from distant tissues (such as detection of ventricular activity on atrial electrodes) or the signal may be attenuated due to disease, ischemia, or tissue necrosis. Further, ablation of one or more identified sites may also be problematic.

To date, such ablations require either substantial trial and error (for example, ablation of all sources of complex fractionated electrograms) or the use of separate mapping and ablation devices (complex mapping systems utilizing multielectrode arrays or baskets may be used to identify an ablation site, but cannot also be used to ablate the tissue). The long term success of treating arrhythmias often depends on the determination of the exact tissue or trigger in the heart causing the arrhythmia so that the malfunctioning tissue can be ablated and the normal rhythm of the heart restored. Ablation of arrhythmias, like atrial fibrillation, whether paroxysmal or chronic, typically involves the simultaneous mapping of a region of cardiac tissue with a multi-electrode catheter in order to identify and ablate tissue sources or drivers of arrhythmias.

Mapping often includes analyzing a displayed electrogram signal in order to identify arrhythmic sites and possible ablation targets. However, in complex electrograms, as in those in patients with atrial fibrillation, the electro gram signals may include several deflections making an accurate real-time determination of target tissue regions cumbersome and ambiguous.

SUMMARY OF THE INVENTION

The present invention advantageously provides a method and system for mapping cardiac tissue. In an exemplary embodiment, the method includes recording a base cardiac electrogram signal at a base electrode for a predetermined amount of time. A plurality of cardiac electrogram signals at a plurality of electrodes other than the base electrode are recorded simultaneously for the predetermined amount of time. The base cardiac electrogram signal is compared with each of the plurality of cardiac electrogram signals. The similarities between the base cardiac electrogram signal and each of the plurality of cardiac electrogram signals is determined. A specific area of cardiac tissue where the base electrode is positioned is mapped based at least in part on the determined similarities.

In another embodiment, a medical system includes a medical device including a base electrode and a plurality of electrodes. A control unit in communication with the base electrode and the plurality of electrodes is included, the control unit being operable to: record a base cardiac electrogram signal at the base electrode for a predetermined amount of time; record a plurality of cardiac electrogram signals at the plurality of electrodes other than the base electrode for the predetermined amount of time; compare the base cardiac electrogram signal with each of the plurality of cardiac electrogram signals; determine similarities between the base cardiac electrogram signal and each of the plurality of cardiac electrogram signals; and map a specific area of cardiac tissue where the base electrode is positioned based at least in part on the determined similarities.

In yet another embodiment, a method for treating arrhythmogenic cardiac tissue is provided. A base cardiac electrogram signal at a base electrode is recorded for a predetermined amount of time. A plurality of cardiac electrogram signals at a plurality of electrodes other than the base electrode are recorded for the predetermined amount of time. The base cardiac electrogram signal is compared with each of the plurality of cardiac electrogram signals. An average correlation coefficient associated with the base cardiac electrogram signal and each of the plurality of cardiac electrogram signals is determined. A specific area of cardiac tissue where the base electrode is positioned is mapped based at least in part on the determined similarities. The average correlation coefficient is analyzed to determine whether the average correlation coefficient has a low value. The specific area of cardiac tissue is identified as arrhythmogenic cardiac tissue when the average correlation coefficient has a low value. A medical device including an ablation element is provided. A closed boundary between the arrhythmogenic cardiac tissue and surrounding cardiac tissue is identified based at least in part on the average correlation coefficient. The medical device is placed in contact with the arrhythmogenic cardiac tissue. The ablation element is activated and substantially all of the arrhythmogenic cardiac tissue within the boundary is ablated.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
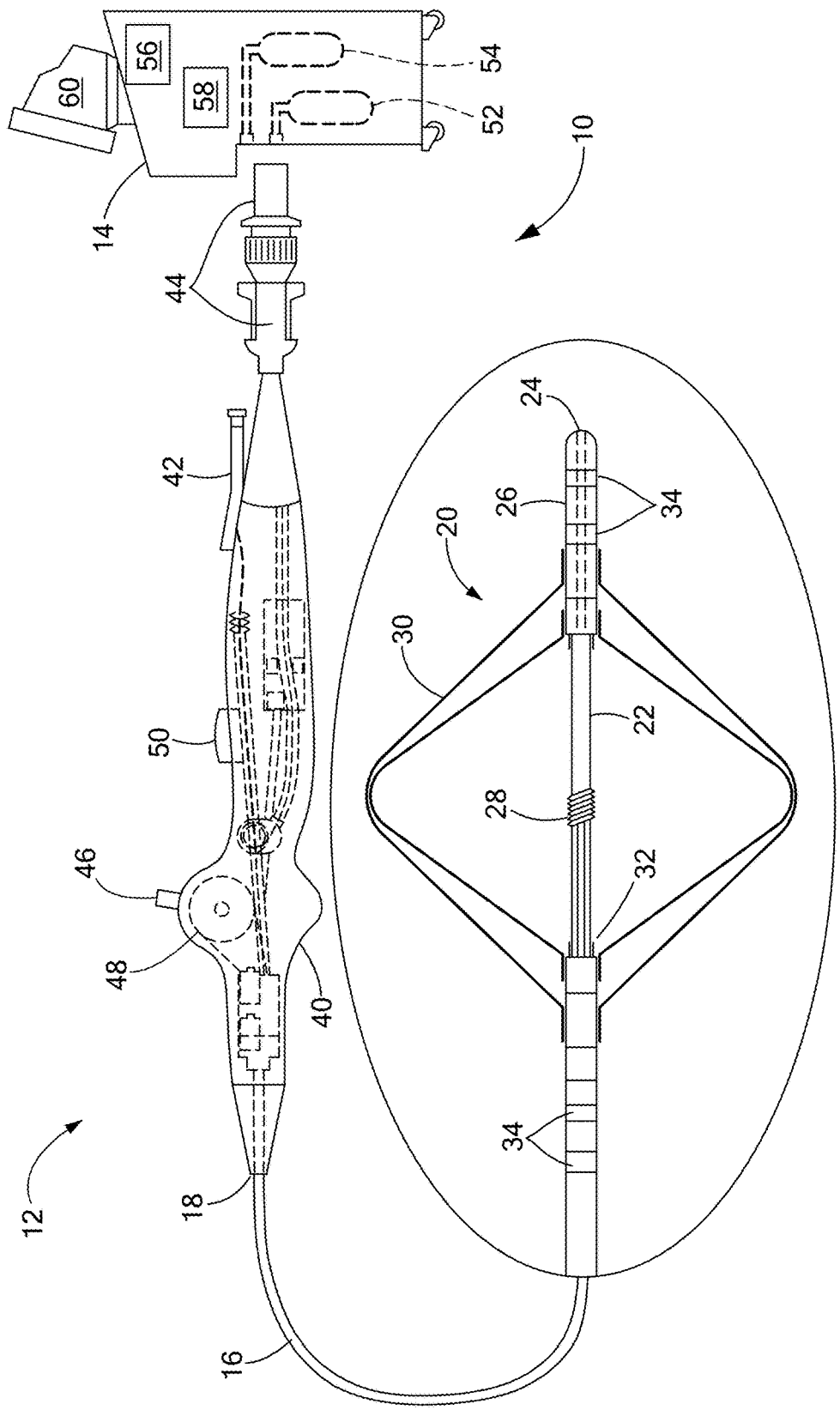
FIG. 1 is an illustration of an example of a medical system constructed in accordance with the principles of the present invention.

Substrate mapping, sequential or simultaneous, may be used to identify arrhythmia circuits that are often the targets of ablation. Sequential mapping may involve using a roving catheter probe to record electrical activity, such as potentials, voltages and electrograms, at a time and point within the myocardium, and then moving the catheter to another point to record electrical activity at a different subsequent time. Simultaneous substrate mapping may involve using a multi-electrode basket catheter to record electrical activity simultaneously over multiple points within a region of mapping. The processing of the recorded electrical information helps identify the arrhythmia circuit.

Conventional mapping involves extracting cardiac activation times by picking up points of deflection or steepest negative slope, and displaying the times over a surface (isochronal map). The patterns during an arrhythmia are observed. For example, an observed pattern may include a rotor around which electrical activation rotates during atrial fibrillation. However, extraction of activation times becomes difficult when the recorded electrogram signals are complex and consist of multiple deflections. Processing of such electrogram signals to identify valid information may also be a time-consuming process, precluding real-time applications of such method during mapping and ablation procedures.

Successful ablation of arrhythmias like AF relies on methods which can efficiently and accurately identify appropriate ablation targets. For example, rotors associated with AF have been shown to be successful ablation targets in trials. However, methods for identification of such rotors require a significant amount of electrogram signal pre-processing, which may prevent the application of such methods universally and/or in real-time. The present disclosure describes methods of creating spatial maps of correlation of electrograms between spatially adjacent electrodes that may be simpler to implement than previous methods. The method disclosed may be more universally applicable than the previous methods for identifying cardiac substrate that can be the target of ablation.

As such, the present invention advantageously provides a system and methods of use thereof for simultaneous cardiac substrate mapping using spatial correlation maps between neighboring unipolar electrograms. In an exemplary embodiment, a two-dimensional ("2D") or three-dimensional ("3D") spatial map of correlation coefficients is created. The correlation coefficient at a given point on the correlation map may be calculated by averaging the simple Pearson correlation coefficients between a unipolar electrogram signal recorded at an electrode positioned at that given point, and simultaneously recorded unipolar electrogram signals at spatially adjacent electrodes. The 2D or 3D correlation map created may be displayed on a display system, wherein the image includes a visual representation of the average of the correlation coefficients calculated.

Regions in the correlation map may be automatically delineated where the correlation coefficient values are less than a pre-specified threshold. The border between regions of high correlation and regions of low correlations may be identified as the defining boundary of the driver/rotor of the arrhythmia circuit. Areas of low correlation within such boundaries may be selected as possible ablation targets for termination of arrhythmias. Such correlation maps may be created over multiple epochs or cycles to identify the movement of the border (rotor). The trajectory of the border between areas of low and high correlation over multiple cycles may also be delineated on a display system to indicate the possible areas of RF/cryo-ablation. In some cases signal morphology may vary from one cycle to another. For example the rotor may not be stable from one cycle to other, but may exhibit some spatial movement. In those cases, the morphology of egm at the site in/near the rotor may change from one cycle to another.

A method of creating spatial maps of correlated electrogram signals from spatially adjacent electrodes belonging to a multi-electrode system to identify arrhythmia circuits and possible ablation targets is provided. An exemplary application may involve identifying rotors associated with atrial fibrillation from electrical recordings obtained from a multi-electrode balloon catheter or a constellation catheter.

Referring now to the drawing figures in which like reference designations refer to like elements, an embodiment of a medical system constructed in accordance with principles of the present invention is shown in FIG. 1 and generally designated as "10." The system 10 generally includes a medical device 12 that may be coupled to a control unit 14 or operating console. The medical device 12 may generally include one or more diagnostic or treatment regions for energetic, therapeutic and/or investigatory interaction between the medical device 12 and a treatment site or region. The diagnostic or treatment region(s) may deliver, for example, cryogenic therapy, radiofrequency energy, or other energetic transfer with a tissue area in proximity to the treatment region(s), including cardiac tissue.

The medical device 12 may include an elongate body 16 passable through a patient's vasculature and/or proximate to a tissue region for diagnosis or treatment, such as a catheter, sheath, or intravascular introducer. The elongate body 16 may define a proximal portion 18 and a distal portion 20, and may further include one or more lumens disposed within the elongate body 16 thereby providing mechanical, electrical, and/or fluid communication between the proximal portion of the elongate body 16 and the distal portion of the elongate body 16, as discussed in more detail below.

The medical device 12 may include a shaft 22 at least partially disposed within a portion of the elongate body 16. The shaft 22 may extend or otherwise protrude from a distal end of the elongate body 16, and may be movable with respect to the elongate body 16 in longitudinal and rotational directions. That is, the shaft 22 may be slidably and/or rotatably moveable with respect to the elongate body 16. The shaft 22 may further define a lumen 24 therein for the introduction and passage of a guide wire. The shaft 22 may include or otherwise be coupled to a distal tip 26 that defines an opening and passage therethrough for the guide wire.

The medical device 12 may further include a fluid delivery conduit 28 traversing at least a portion of the elongate body and towards the distal portion. The delivery conduit 28 may be coupled to or otherwise extend from the distal portion of the elongate body 16, and may further be coupled to the shaft 22 and/or distal tip of the medical device 12. The fluid delivery conduit 28 may define a lumen therein for the passage or delivery of a fluid from the proximal portion of the elongate body 16 and/or the control unit 14 to the distal portion and/or treatment region of the medical device 12. The fluid delivery conduit 28 may further include one or more apertures or openings therein, to provide for the dispersion or directed ejection of fluid from the lumen to an environment exterior to the fluid delivery conduit 28.

The medical device 12 may further include one or more expandable elements 30 at the distal portion of the elongate body 16. The expandable element 30 may be coupled to a portion of the elongate body 16 and also coupled to a portion of the shaft 22 and/or distal tip 26 to contain a portion of the fluid delivery conduit 28 therein. The expandable element 30 defines an interior chamber or region that contains coolant or fluid dispersed from the fluid delivery conduit 28, and may be in fluid communication with an exhaust lumen 32 defined by or included in the elongate body 16 for the removal of dispersed coolant from the interior of the expandable element 30. The expandable element 30 may further include one or more material layers providing for puncture resistance, radiopacity, or the like.

Figure 2:
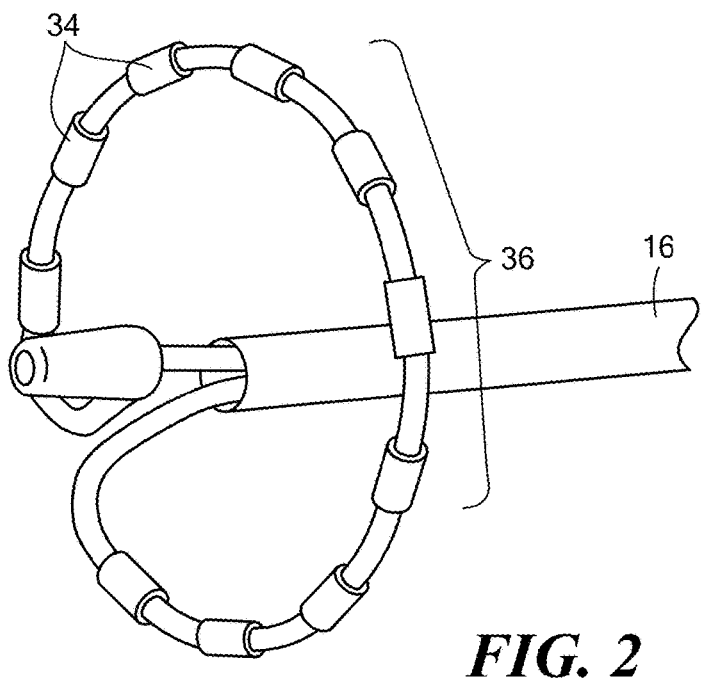
FIG. 2 is an illustration of an example of a medical device assembly constructed in accordance with the principles of the present invention.
Figure 3:
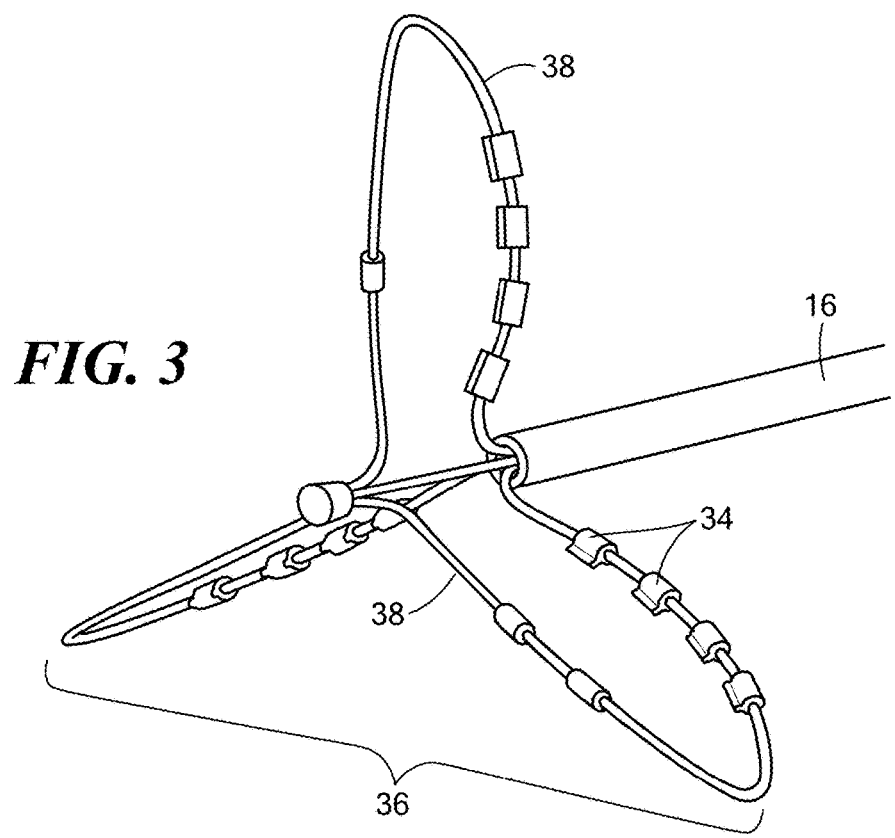
FIG. 3 is another illustration of an example of a medical device assembly constructed in accordance with the principles of the present invention.
Figure 4:
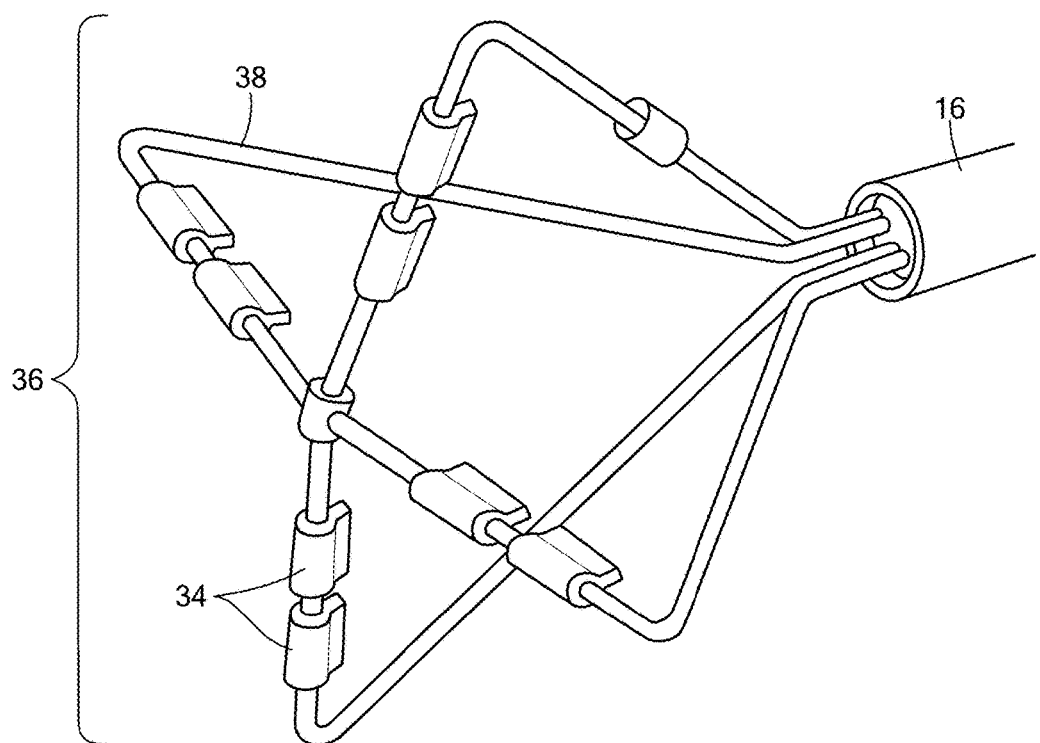
FIG. 4 is still another illustration of an example of a medical device assembly constructed in accordance with the principles of the present invention.
Figure 5:
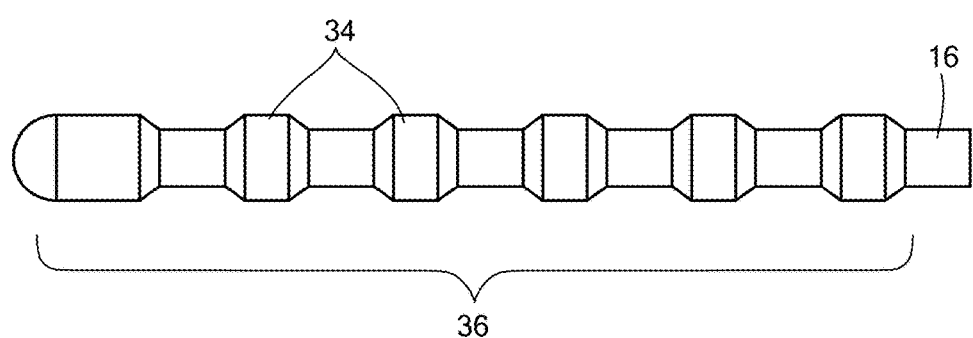
FIG. 5 is yet another illustration of an example of a medical device assembly constructed in accordance with the principles of the present invention.

The medical device 12 may further include one or more electrically-conductive segments or electrodes 34 positioned on or about the elongate body for conveying an electrical signal, current, or voltage to a designated tissue region and/or for measuring, recording, or otherwise assessing one or more electrical properties or characteristics of surrounding tissue. The electrodes 34 may be configured in a myriad of different geometric configurations or controllably deployable shapes, and may also vary in number to suit a particular application, targeted tissue structure or physiological feature. For example, as shown in FIG. 1, the electrodes 34 may include a first pair proximate to the expandable element and a second electrode pair distal to the expandable element. Alternative electrode configurations of the medical device 12 are illustrated in FIGS. 2-5. FIG. 2 includes an electrode array 36 configurable into a looped or substantially circular configuration. The electrode array 36 in FIG. 3 includes a plurality of arms 38, with the electrodes 34 positioned in a proximal-facing direction or orientation on the arms 38. FIG. 4 also includes a plurality of extendable or deployable arms 38 having a plurality of electrodes 34 in a square-like or "X"-shaped configuration. Turning to FIG. 5, a plurality of electrodes 34 are shown in a substantially linear array 36 extending along a portion of the elongate body 16 of the medical device 12. In each of these embodiments shown in FIGS. 2-5, the electrodes 34 may be positioned on the medical device 12 substantially equidistant from an adjacent electrode 34 in the array or may be variable distances from each adjacent electrode 34.

Each electrode 34 may be electrically coupled to an output portion of a radiofrequency signal generator, and each electrode 34 may also include a sensor, such as a thermocouple, an electrical conductivity sensor, a spectrometer, a pressure sensor, a fluid flow sensor, a pH sensor, and/or a thermal sensor (not shown) coupled to or in communication with the electrodes. The sensors may also be in communication with a feedback portion of the control unit 14 to trigger or actuate changes in operation when predetermined sequences, properties, or measurements are attained or exceeded.

Referring again to FIG. 1, the medical device 12 may include a handle 40 coupled to the proximal portion of the elongate body 16. The handle 40 can include circuitry for identification and/or use in controlling of the medical device 12 or another component of the system. Additionally, the handle 40 may be provided with a fitting 42 for receiving a guide wire that may be passed into the guide wire lumen 24. The handle 40 may also include connectors 44 that are mateable to the control unit 14 to establish communication between the medical device 12 and one or more components or portions of the control unit 14.

The handle 40 may also include one or more actuation or control features that allow a user to control, deflect, steer, or otherwise manipulate a distal portion of the medical device 12 from the proximal portion of the medical device 12. For example, the handle 40 may include one or more components such as a lever or knob 46 for manipulating the elongate body 16 and/or additional components of the medical device 12. For example, a pull wire 48 with a proximal end and a distal end may have its distal end anchored to the elongate body 16 at or near the distal portion 20. The proximal end of the pull wire 48 may be anchored to an element such as a cam in communication with and responsive to the lever 46. The medical device 12 may include an actuator element 50 that is movably coupled to the proximal portion of the elongate body 16 and/or the handle 40 for the manipulation and movement of a portion of the medical device 12, such as the shaft 22, and/or one or more portions of the electrode assemblies described above, for example.

The system 10 may include one or more treatment sources coupled to the medical device for use in an operative procedure, such as tissue ablation, for example. The control unit 14 may include a fluid supply 52 including a coolant, cryogenic refrigerant, or the like, an exhaust or scavenging system (not shown) for recovering or venting expended fluid for re-use or disposal, as well as various control mechanisms. In addition to providing an exhaust function for the fluid or coolant supply 52, the control unit 14 may also include pumps, valves, controllers or the like to recover and/or re-circulate fluid delivered to the handle 40, the elongate body 16, and/or the fluid pathways of the medical device 12. A vacuum pump 54 in the control unit 14 may create a low-pressure environment in one or more conduits within the medical device 12 so that fluid is drawn into the conduit(s)/lumen(s) of the elongate body 16, away from the distal portion 20 and towards the proximal portion 18 of the elongate body 16.

The control 14 unit may include a radiofrequency generator or power source 56 as a treatment or diagnostic mechanism in communication with the electrodes 34 of the medical device 12. The radiofrequency generator 56 may have a plurality of output channels, with each channel coupled to an individual electrode 34. The radiofrequency generator 56 may be operable in one or more modes of operation, including for example: (i) bipolar energy delivery between at least two electrodes on the medical device within a patient's body, (ii) monopolar or unipolar energy delivery to one or more of the electrodes 34 on the medical device 12 within a patient's body and through a patient return or ground electrode (not shown) spaced apart from the electrodes 34 of the medical device 14, such as on a patient's skin for example, and (iii) a combination of the monopolar and bipolar modes.

The system 10 may further include one or more sensors to monitor the operating parameters throughout the system, including for example, pressure, temperature, flow rates, volume, power delivery, impedance, or the like in the control unit 14 and/or the medical device 12, in addition to monitoring, recording or otherwise conveying measurements or conditions within the medical device 12 or the ambient environment at the distal portion of the medical device 12. The sensor(s) may be in communication with the control unit 14 for initiating or triggering one or more alerts or therapeutic delivery modifications during operation of the medical device 12. One or more valves, controllers, or the like may be in communication with the sensor(s) to provide for the controlled dispersion or circulation of fluid through the lumens/fluid paths of the medical device 12. Such valves, controllers, or the like may be located in a portion of the medical device 12 and/or in the control unit 14.

The control unit 14 may include one or more controllers, processors, and/or software modules containing instructions or algorithms to provide for the automated operation and performance of the features, sequences, calculations, or procedures described herein. For example, the control unit 14 may include a signal processing unit 58 to measure one or more electrical characteristics between the electrodes 34 of the medical device 12. An excitation current may be applied between one or more of the electrodes 34 on the medical device 12 and/or a patient return electrode, and the resulting voltage, impedance, or other electrical properties of the target tissue region may be measured, for example, in an electrogram, as described in more detail below. Unipolar electrograms ("egms") may be recorded with the mapping electrode 34 as the positive electrode, and another electrode 34 on the body surface or remote from the field or cardiac excitation as the negative electrode. The control unit may further include a display 60 to display the various recorded signals and measurement, for example, an electrogram.

Figure 6:
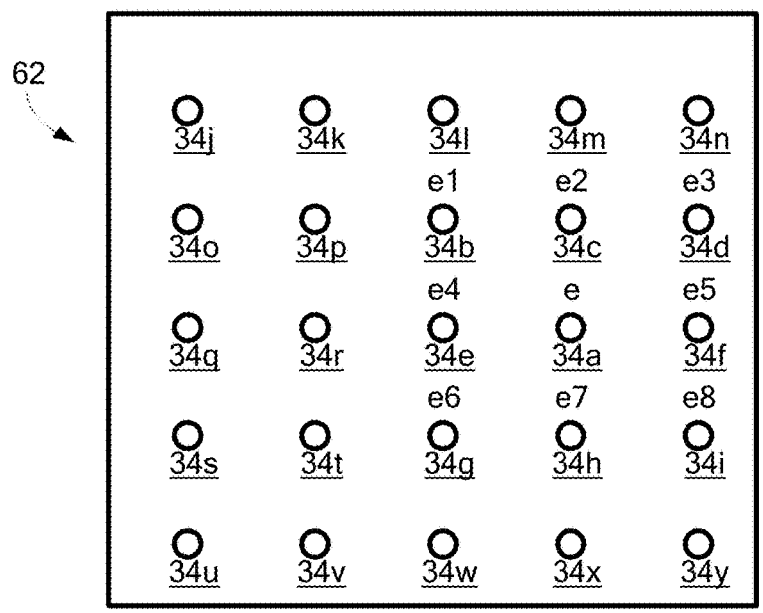
FIG. 6 is a block diagram of an electrode mapping grid in accordance with the principles of the present invention.

FIG. 6 is a block diagram of an exemplary electrode mapping grid 62, including base electrode e 34a, electrode e1 34b, electrode e2 34c, electrode e3 34d, electrode e4 34e, electrode e5 34f, electrode e6 34g, electrode e7 34h and electrode e8 34i. Additionally, electrode mapping grid 62 includes electrodes 34j, 34k, 34l, 34m, 34n, 34o, 34p, 34q, 34r, 34s, 34t, 34u, 34v, 34w, 34x and 34y. Electrodes 34 within a certain predefined physical distance d of base electrode e 34a may be referred to as neighbor/neighboring electrodes 34. The distance d can be any value between one millimeter and twenty millimeters.

The exact distance may depend on the particular design and inter-electrode spacing of the medical device 12, e.g., the mapping catheter. In the exemplary electrode mapping grid 62, the distance between each electrode 34 is two millimeters. As such, for a pre-defined value of d of two millimeters, the electrodes 34 that are neighbors of base electrode e 34a include electrodes e1 34b, electrode e2 34c, electrode e3 34d, electrode e4 34e, electrode e5 34f, electrode e6 34g, electrode e7 34h and electrode e8 34i.

In an exemplary embodiment, a base cardiac electrogram signal is recorded at the base electrode e 34a for a predetermined amount of time, which may be the length of an arrhythmia cycle. Electrogram signals at electrode e1 34b, electrode e2 34c, electrode e3 34d, electrode e4 34e, electrode e5 34f, electrode e6 34g, electrode e7 34h and electrode e8 34i are recorded simultaneously to the recording of the base cardiac electrogram signal for the same predetermined amount of time.

The electrogram signals may be recorded for several milliseconds. For example, the electrogram signals may be recorded for 100 ms to 350 ms, i.e., the length of time the electrogram signal is recorded may equal the length of time of an arrhythmia cycle, which is usually 100 ms to 350 ms. The recording may be performed over multiple arrhythmia cycles, the correlation map may be created for each cycle, and spatial display of the maps over multiple cycles may be presented to track the movement of the boundary between areas of low and high correlation.

The base cardiac electrogram signal and the plurality of cardiac electrogram signals may be recorded simultaneously. Recording the base cardiac electrogram signal at the same time as the plurality of electrogram signals from the neighboring electrodes 34 may ensure that all of the electrogram signals correspond to a particular arrhythmia cycle. Correlation maps may be constructed over each cycle and analysis of correlation-maps may be performed over multiple cycles to track the trajectory of the areas of low and high correlation over multiple cycles.

In order to map the location where electrode e 34a is positioned, the electrogram signal recorded at base electrode e 34a is compared to each of the other electrogram signals of the other electrodes 34, i.e., to each electrogram signal from electrode e1 34b, electrode e2 34c, electrode e3 34d, electrode e4 34*e*, electrode e5 34*f*, electrode e6 34*g*, electrode e7 34*h* and electrode e8 34*i*.

In this exemplary embodiment, only the electrogram signals from neighboring electrodes 34 that are neighbors to electrode e 34*a* (e.g., electrode e1 34*b*, electrode e2 34*c*, electrode e3 34*d*, electrode e4 34*e*, electrode e5 34*f*, electrode e6 34*g*, electrode e7 34*h* and electrode e8 34*i*) are compared to the base cardiac electrogram signal from base electrode e 34*a*. However, the invention is not limited to such, as any number of electrogram signals from any number of electrodes 34 may be compared to any electrogram signal from any electrode 34.

The similarities between the electrogram signals are determined, i.e., the similarities between the base cardiac electrogram signal and each of the plurality of cardiac electrogram signals from electrode e1 34*b*, electrode e2 34*c*, electrode e3 34*d*, electrode e4 34*e*, electrode e5 34*f*, electrode e6 34*g*, electrode e7 34*h* and electrode e8 34*i* are determined. For example, the similarities between (i) the base cardiac electrogram signal and the cardiac electrogram signal from electrode e1 34*b* is determined; (ii) the base cardiac electrogram signal and the cardiac electrogram signal from electrode e2 34*c* is determined; (iii) the base cardiac electrogram signal and the cardiac electrogram signal from electrode e3 34*d* is determined; (iv) the base cardiac electrogram signal and the cardiac electrogram signal from electrode e4 34*e* is determined; (v) the base cardiac electrogram signal and the cardiac electrogram signal from electrode e5 34*f* is determined; (vi) the base cardiac electrogram signal and the cardiac electrogram signal from electrode e6 34*g* is determined; (vii) the base cardiac electrogram signal and the cardiac electrogram signal from electrode e7 34*h* is determined; and (viii) the base cardiac electrogram signal and the cardiac electrogram signal from electrode e8 34*i* is determined.

In an exemplary embodiment, the similarities between the electrogram signals are determined using any method that can measure and establish the morphological similarities of signals, such as wavelet algorithms, correlation, etc. The determined similarities and/or differences between the electrogram signals are used to map cardiac tissue. A representation, such as a visual depiction, of the determined similarities and/or differences between the electrogram signals is associated with a location in a two-dimensional ("2D") or three-dimensional ("3D") spatial map of cardiac tissue.

By way of example, if the base cardiac electrogram signal from the base electrode e 34*a* is compared against each of the electrogram signals from electrode e1 34*b*, electrode e2 34*c*, electrode e3 34*d*, electrode e4 34*e*, electrode e5 34*f*, electrode e6 34*g*, electrode e7 34*h* and electrode e8 34*i* (for a total of eight comparisons), a specific area of cardiac tissue where the base electrode e 34*a* is positioned is mapped based at least in part on the determined similarities.

In an exemplary embodiment, correlation techniques may be used to compare the electrogram signals and determine the similarities between the electrogram signals. A correlation value between the base cardiac electrogram signal and each of the electrogram signals from electrode e1 34*b*, electrode e2 34*c*, electrode e3 34*d*, electrode e4 34*e*, electrode e5 34*f*, electrode e6 34*g*, electrode e7 34*h* and electrode e8 34*i* may be determined. As such, for this example, a total of eight correlation values are calculated. In order to create a physical correlation map, the average of the correlation values is mapped to the location of the base electrode 34*a*.

The correlation value, e.g., coefficient, at a given point on a two-dimensional ("2D") or three-dimensional ("3D") spatial map may be computed by the average of the simple Pearson correlations between the unipolar electrogram signal recorded at that point and simultaneously recorded unipolar electrograms at one or more spatially adjacent electrodes 30. A correlation coefficient may be a single number that describes the degree of relationship between two variables, e.g., two electrogram signals. The average correlation coefficient mapped this way represents how electrically similar the mapping location is relative to the neighboring substrate. An arrhythmogenic substrate is usually created by spatial dissimilarities in electrical properties of tissue, for example, a conduction block which may be functional and/or anatomic.

The Pearson product-moment correlation coefficient (sometimes referred to as the PPMCC or PCC or Pearson's r) is a measure of the correlation (linear dependence) between two variables X and Y, having a value between +1 and −1 inclusive. The Pearson correlation coefficient is widely used as a measure of the strength of linear dependence between two variables. The Pearson's correlation coefficient between two variables is defined as the covariance of the two variables divided by the product of their standard deviations. The definition involves a 'product moment,' i.e., the mean (the first moment about the origin) of the product of the mean-adjusted random variables.

Pearson's correlation coefficient when applied to a sample is referred to as the sample correlation coefficient or the sample Pearson correlation coefficient ("r"). The formula for r is:

$$r = \frac{\sum_{i=1}^{n}(X_i - \overline{X})(Y_i - \overline{Y})}{\sqrt{\sum_{i=1}^{n}(X_i - \overline{X})^2}\sqrt{\sum_{i=1}^{n}(Y_i - \overline{Y})^2}}$$

For example, when using the above formula to calculate the correlation coefficient for the location where base electrode e 34*a* is located, X represents a sample value of the base cardiac electrogram signal recorded at base electrode e 34*a* at a time, and Y represents a sample value of one of the plurality of cardiac electrogram signals at the same time. For instance, one of the plurality of electrogram signals may be the electrogram signal recorded at one of electrode e1 34*b*, electrode e2 34*c*, electrode e3 34*d*, electrode e4 34*e*, electrode e5 34*f*, electrode e6 34*g*, electrode e7 34*h* and electrode e8 34*i*. The letter 'n' represents the number of sample values obtained from the base cardiac electrogram signal or one of the plurality of electrogram signals for a predetermined amount of time (usually equal to one cycle-length of the arrhythmia).

With respect to the value of 'n', if the electrogram signals are 1 kHz signals, and the electrogram signals are recorded for 300 ms, then n would be 300, i.e., the number of sample values obtained from the base cardiac electrogram signal may be approximately 300 samples, and the number of sample values obtained from one of the plurality of electrogram signals may also be approximately 300 samples. The number of samples obtained may correspond to one arrhythmia cycle at an electrode 34.

An equivalent expression gives the correlation coefficient as the mean of the products of the standard scores. The formula for the sample Pearson correlation coefficient r, based on a sample of paired data ($X_i$, $Y_i$), is shown below:

$$r = \frac{1}{n-1} \sum_{i=1}^{n} \left( \frac{X_i - \overline{X}}{s_X} \right) \left( \frac{Y_i - \overline{Y}}{s_Y} \right)$$

where $\frac{X_i - \overline{X}}{s_X}$, $\overline{X}$, and $s_X$ are the standard score, sample mean of X (i.e., the sample mean of the total number of samples), and sample standard deviation, respectively.

The correlation coefficient ranges from −1 to 1. A correlation coefficient value of 1 implies that a linear equation describes the relationship between X and Y perfectly, with all data points lying on a line where Y increases as X increases, i.e., there is a perfect positive correlation between two variables. A correlation coefficient value of −1 implies that all data points lie on a line for which Y decreases as X increases, i.e., that there is a perfect negative correlation between two variables. A value of 0 implies that there is no linear correlation between the variables X and Y. Correlation values are seldom exactly 1, 0 or −1, as most of the time the correlation values fall somewhere in between 1 and −1. The closer the correlation value approaches zero, the greater the variation.

The correlation between variables is a measure of how well the variables are related, such as the linear relationship between two variables. For example an exemplary high correlation value may be predefined as 0.9 to 1.0; an exemplary medium correlation value may be predefined as 0.76 to 0.9; and an exemplary low correlation value may be predefined as any value equal to or below 0.75. A relationship between two variables exists when changes in one variable tend to be accompanied by consistent and predictable changes in the other variable.

The direction of the relationship is measured by the sign of the correlation, whether it is positive (+) or negative (−). A positive correlation means that the two variables tend to change in the same direction, as one increases, the other variable also increases. A negative correlation means that the two variables tend to change in opposite directions, e.g., as one increases the other variable tends to decrease. The degree of the relationship between the variables, i.e., the strength or consistency of the relationship, is measured by the numerical value of the correlation. A value of 1 indicates a perfect relationship and a value of 0 indicates no relationship. However, in an exemplary embodiment, for the purpose of this invention, similarity may be determined based on a high positive value of correlation only. For example, a high negative correlation value (e.g. −0.8), a low negative correlation value (e.g. −0.2), and a low positive correlation value (e.g. 0.2) may be all regarded as indicators of dissimilarity.

A correlation technique may be used to compare and determine the similarities between electrogram signals. As such, in an exemplary embodiment, a plurality of correlation coefficients, wherein each of the plurality of correlation coefficients corresponds to the base cardiac electrogram signal and a different one of the plurality of cardiac electrogram signals may be determined. For instance, the following correlation coefficients may be determined: a first correlation coefficient between the base cardiac electrogram signal from base electrode e 34a and the electrogram signal from electrode e1 34b; a second correlation coefficient between the base cardiac electrogram signal and the electrogram signal from electrode e2 34c; a third correlation coefficient between the base cardiac electrogram signal and the electrogram signal from electrode e3 34d; a fourth correlation coefficient between the base cardiac electrogram signal and the electrogram signal from electrode e4 34e; a fifth correlation coefficient between the base cardiac electrogram signal and the electrogram signal from electrode e5 34f; a sixth correlation coefficient between the base cardiac electrogram signal and the electrogram signal from electrode e6 34g; a seventh correlation coefficient between the base cardiac electrogram signal and the electrogram signal from electrode e7 34h; and an eighth correlation coefficient between the base cardiac electrogram signal and the electrogram signal from electrode e8 34i.

The plurality of correlation coefficients determined, e.g., the first, second, third, fourth, fifth, sixth, seventh and eighth correlation coefficients, are averaged. For instance, the first, second, third, fourth, fifth, sixth, seventh and eighth correlation coefficients may be 0.8, 0.4, 0.9, 0.7, 0.7, 0.8, 0.9 and 0.8 respectively. In this case, the average of the plurality of correlation coefficients is equal to 0.75 (e.g., (0.8+0.4+0.9+0.7+0.7+0.8+0.9+0.8)/8). The average of the plurality of correlation coefficients is associated to the specific area of cardiac tissue where the base electrode e 34a is positioned.

As such, the specific area of the cardiac tissue where the based electrode e 34a is positioned is mapped to the average of the plurality of correlation coefficients, which in this example is the value 0.75. An image corresponding to a specific area of cardiac tissue, wherein the image includes a visual representation of the average of the determined similarities between the base cardiac electrogram signal and each of the plurality of cardiac electrogram signals may be displayed on a display system.

The average correlation coefficient can be computed for each electrode 34 positioned at a location where mapping is desired. For example, in order to map a different area of cardiac tissue, such as the neighbor area (neighbor area to the specific area where base electrode e 34a is positioned) where neighbor electrode e1 34b is positioned, a determination is made as to which electrodes 34 are neighbors to neighbor electrode e1 34b. In this example, the neighbors of electrode e1 34b are: base electrode e 34a, electrode e2 34c, e4 34e, electrode 34r, electrode 34p, electrode 34k, electrode 34l and electrode 34m, since these electrodes 34 are located within two millimeters from electrode e1 34b.

A neighbor cardiac electrogram signal at electrode e1 34b is recorded. Additionally, electrogram signals at the electrodes that are neighbors to e1 34b are also recorded (e.g., base electrode e 34a, electrode e2 34c, e4 34e, electrode 34r, electrode 34p, electrode 34k, electrode 34l and electrode 34m). The neighbor cardiac electrogram signal recorded at electrode e1 34b (which is a neighbor of electrode e 34a) is compared to each of the electrogram signals recorded at base electrode e 34a, electrode e2 34c, e4 34e, electrode 34r, electrode 34p, electrode 34k, electrode 34l and electrode 34m.

For example, the neighbor cardiac electrogram signal recorded at electrode e1 34b is compared to the base cardiac electrogram signal recorded at base electrode e 34a; the neighbor cardiac electrogram signal recorded at electrode e1 34b is compared to the electrogram signal recorded at electrode e2 34c; the neighbor cardiac electrogram signal recorded at electrode e1 34b is compared to the electrogram signal recorded at electrode e4 34e; the neighbor cardiac electrogram signal recorded at electrode e1 34b is compared to the electrogram signal recorded at electrode 34r; the neighbor cardiac electrogram signal recorded at electrode e1

34b is compared to the electrogram signal recorded at electrode 34p; the neighbor cardiac electrogram signal recorded at electrode e1 34b is compared to the electrogram signal recorded at electrode 34k; the neighbor cardiac electrogram signal recorded at electrode e1 34b is compared to the electrogram signal recorded at electrode 34l; and the neighbor cardiac electrogram signal recorded at electrode e1 34b is compared to the electrogram signal recorded at electrode 34m.

The similarities between the neighbor cardiac electrogram signal from neighbor electrode e1 34b and each of the electrogram signals recorded at base electrode e 34a, electrode e2 34c, e4 34e, electrode 34r, electrode 34p, electrode 34k, electrode 34l and electrode 34m are determined. Correlation coefficients may be used to determine the similarities between: (i) the neighbor electrogram signal from neighbor electrode e1 34b and the base cardiac electrogram signal from electrode e 34a; and (ii) the neighbor cardiac electrogram signal from neighbor electrode e1 34b and each of the plurality of cardiac electrogram signals other than the neighbor cardiac electrogram signal (e.g. the electrogram signals recorded at electrode e2 34c, e4 34e, electrode 34r, electrode 34p, electrode 34k, electrode 34l and electrode 34m).

In an exemplary embodiment, to determine the similarities between the neighbor cardiac electrogram signal and the plurality of electrogram signals, a plurality of neighbor correlation coefficients are determined, wherein each of the plurality of neighbor correlation coefficients corresponds to the neighbor electrogram signal from neighbor electrode e1 34b and one of (i) a different one of the plurality of cardiac electrogram signals from electrode e2 34c, e4 34e, electrode 34r, electrode 34p, electrode 34k, electrode 34l and electrode 34m; and (ii) the base cardiac electrogram signal.

For example, the following neighbor correlation coefficients can be determined: a ninth correlation coefficient between the electrogram signal from neighbor electrode e1 34b and the base electrogram signal from electrode e 34a; a tenth correlation coefficient between the electrogram signal from neighbor electrode e1 34b and the electrogram signal from electrode e2 34c; an eleventh correlation coefficient between the electrogram signal from neighbor electrode e1 34b and the electrogram signal from electrode e4 34e; a twelfth correlation coefficient between the electrogram signal from neighbor electrode e1 34b and the electrogram signal from electrode 34r; a thirteenth correlation coefficient between the electrogram signal from neighbor electrode e1 34b and the electrogram signal from electrode 34p; a fourteenth correlation coefficient between the electrogram signal from neighbor electrode e1 34b and the electrogram signal from electrode 34k; a fifteenth correlation coefficient between the electrogram signal from neighbor electrode e1 34b and the electrogram signal from electrode 34l; and a sixteenth correlation coefficient between the electrogram signal from neighbor electrode e1 34b and the electrogram signal from electrode 34m.

The plurality of neighbor correlation coefficients (e.g., the ninth, the tenth, the eleventh, the twelfth, the thirteenth, the fourteenth, the fifteenth and the sixteenth correlation coefficients) are averaged, and the average of the plurality of neighbor correlation coefficients is associated to the neighbor area of cardiac tissue where the neighbor electrode 1b 34b is positioned. For example, if the average of the correlation coefficient is 0.8, the location where electrode e1 34b is positioned will be mapped to the value of 0.8. The method is repeated for each electrode 34, until a correlation map 64 showing a visual depiction of the average correlation coefficient for each location where electrodes 34 of interest are positioned is created.

Figure 7:
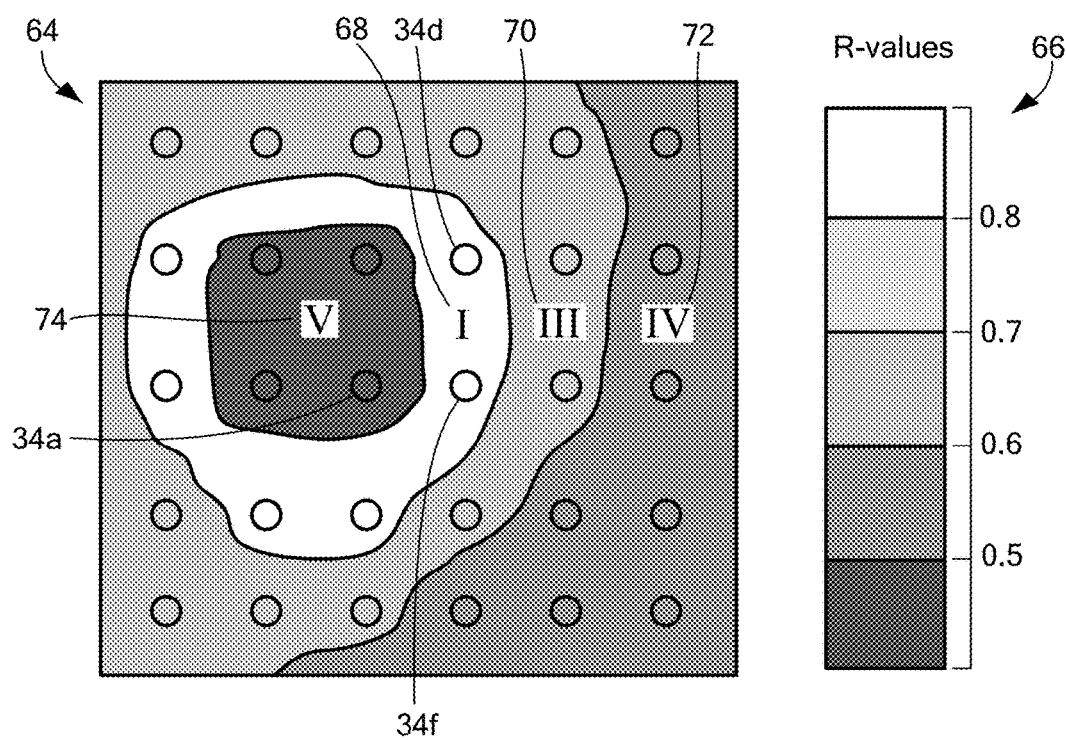
FIG. 7 is a graph of an exemplary correlation map constructed in accordance with the principles of the present invention.

Referring now to FIG. 7, an exemplary spatial 2D correlation map 64 of cardiac tissue is shown. The correlation map 64 can be generated using correlation coefficients associated with simultaneous electrogram signals obtained at neighboring unipolar electrodes 34 for a given arrhythmia cycle. The color key 66 includes an exemplary range of average correlation coefficient values that may be associated with an area where an electrode 34 is positioned, and associates the average correlation coefficient values with a color. In this way, the average correlation coefficient value imputed to an area may be visually represented by a color in the correlation map 64.

In an exemplary embodiment, the cardiac tissue mapped may include different areas, such as area I 68, area II, area III 70, area IV 72 and area V 74. The exemplary correlation map 64 uses grayscale to indicate the different values of the average correlation coefficients associated to each area. For example, since area V 74 is associated with an average correlation coefficient that is low, e.g., less than 0.5, area V 74 may be visually depicted on the correlation map 64 as an area having the darkest shade. Area IV 72 is associated with an average correlation coefficient that is 0.5 or more but less than 0.6 and may be visually depicted on the correlation map 64 as an area with a shade that is less dark than the shade of area V 74. Area III 70 is associated with an average correlation coefficient that is 0.6 or more, but less than 0.7, and may be visually represented on the correlation map 64 as an area having a light shade. Area II may be associated with an average correlation coefficient that is 0.7 or more, but less than 0.8, and may be visually represented on the correlation map 64 as an area having a lighter shade than area III 70. Area I 68 is associated with a high average correlation coefficient that is 0.8 or more and may be represented as the area having the lightest shade.

Since area V 74 has the darkest shading, this indicates that the average correlation coefficients corresponding to the electrogram signals recorded at electrodes 34 positioned in area V 74 have a value below 0.5. The low correlation coefficient may suggest that area V 74 includes damaged or arrhythmogenic cardiac tissue. The determination as to whether a specific area of cardiac tissue is damaged or arrhythmogenic or not depends on whether or not the electro gram signal recorded at that specific area of cardiac tissue is similar to the electro gram signals recorded at neighboring electrodes 34. If the electrogram signal recorded at that specific area of cardiac tissue is similar to the electrogram signals recorded at neighboring electrodes 34, then the specific area will probably not include damaged or arrhythmogeniccardiac tissue, as the high degree of similarity between the electrogram signals is indicated by a high correlation between the electrogram signals. However, if the electrogram signal recorded at that specific area of cardiac tissue is not similar to the electrogram signals recorded at neighboring electrodes 34, then the specific area would probably include damaged or arrhythmogenic cardiac tissue, i.e., there is a low correlation between the electrogram signals.

In this exemplary embodiment, the comparison of the base cardiac electrogram signal recorded at base electrode e 34a in area V 74 to the electrogram signals recorded at electrodes 34 that are neighbors to base electrode e 34a, revealed that the correlation between the base cardiac electrogram signal and the plurality of neighboring electrogram signals is low. The electrogram signals were compared using Pearson correlation coefficients. The correlation computations resulted in Pearson correlation coefficients with an average value below 0.5, such as for example 0.45. The average correlation coefficient is mapped to the location where base electrode e 34a is positioned in area V 74, i.e., area V 74 is associated with a visual representation of an average correlation coefficient having a value below 0.5. As such, mapping is achieved by associating the value of an average correlation coefficient to an area in the correlation map 64 corresponding to cardiac tissue where an electrode 34 is positioned.

In an exemplary embodiment, a determination may be made as to whether the mapping value of the area V 74 is similar to the mapping value of the neighbor area I 68. For instance, a determination may be made as to whether a correlation coefficient associated with area V 74 is similar to a correlation coefficient associated with area I 68. If it is determined that the mapping value of the area V 74 of cardiac tissue is similar to the mapping value of the neighbor area I 68, then it may be likely that neither area V 74 or the neighbor area I 68 include damaged or arrhythmogenic cardiac tissue. Else, if it is determined that the mapping value of the area V 74 of cardiac tissue is not similar to the mapping value of the neighbor area I 68, then it may be determined that one of area V 74 and the neighbor area I 68 includes damaged or arrythmogenic cardiac tissue.

Different colors may be used for different areas of correlation map 64 to indicate the value of the average correlation coefficient in each area. For example, in one embodiment, area V having a low average correlation coefficient, such as a correlation coefficient having a value below 0.5, may be visually represented as a red area. Area IV associated with an average correlation coefficient having a value of 0.5 or more, but less than 0.6 may be visually represented in the correlation map 64 as a yellow area. Area III associated with an average correlation coefficient with a value of 0.6 or more, but less than 0.7 may be visually depicted in the correlation map 64 as a light green area. Area II associated with an average correlation coefficient having a value of 0.7 or more, but less than 0.8 may be visually represented in the correlation map 64 as a darker green area. Area I having an average correlation coefficient that has a value of 0.8 or above may be visually represented in the correlation map 64 as a blue area.

Simultaneous cardiac substrate mapping includes the recording of a plurality of neighboring electrogram signals at substantially the same time, i.e., the same epoch. Since the electrogram signals are recorded at different electrodes 34 for the same arrhythmia cycle, i.e., the same epoch, there may be no need to align the electrogram signals in order to properly compare the electrogram signals. Data obtained over multiple epochs may be used to create the correlation map 64 in order to ensure consistency in areas of discontinuous conduction (e.g., rotor) over different epochs and as a measure of stability of the arrhythmia cycle.

It is common to compare electrogram signals recorded at different times by aligning them with each other. During alignment, an electrogram signal taken at a time is aligned with another electrogram signal taken at a different time. For instance, the peaks, e.g., the maximum values of an electrogram signal, may be aligned with the peaks of another electrogram signal. Alignment is difficult for complex electrogram signals, as these signals may have multiple deflections and peaks, making it challenging to ascertain which peaks of an electrogram signal should be aligned with which peaks of another electrogram signal. This complexity may result in the alignment process aligning peaks and phases which do not correspond to each other. In an exemplary embodiment, the methods described herein may not need alignment of the electrogram signals, given that the electrogram signals from multiple electrodes 34 are obtained simultaneously, at the same time or at substantially the same time.

Figure 8:
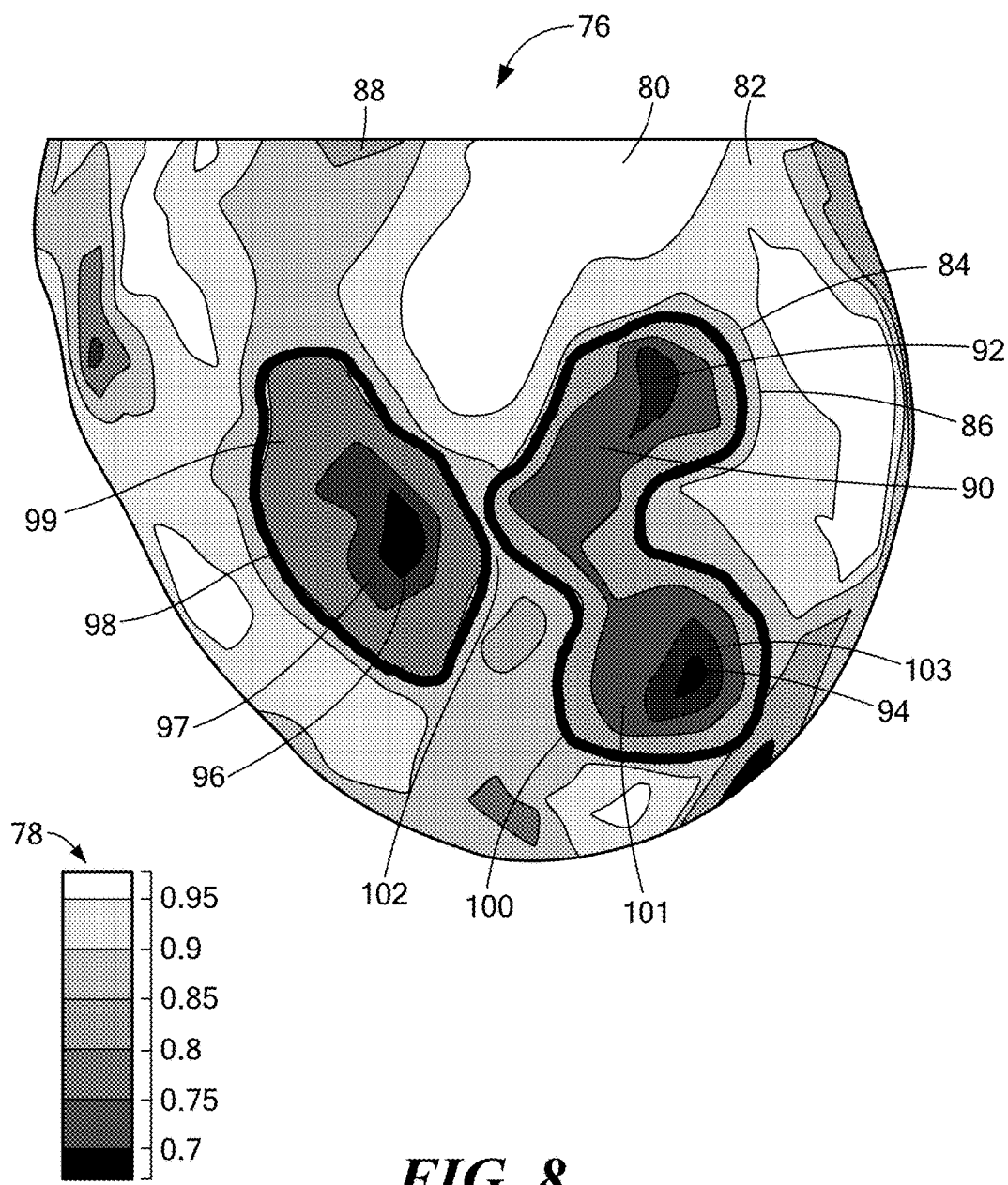
FIG. 8 is a graph of another exemplary cardiac correlation map constructed in accordance with the principles of the present invention.

FIG. 8 shows an exemplary canine infarct model correlation map 76 and color key 78. The correlation map 76 may be created employing the methods described herein for simultaneous cardiac substrate mapping using spatial correlation maps between electrograms from neighboring unipolar electrodes. The electrogram signals utilized to create exemplary correlation map 76 may be recorded using electrodes 34 positioned directly on the epicardial layer of a ventricle. The correlation map 76 may allow the visual identification of abnormal cardiac substrate, e.g., areas where a possible rotor may be located. Specifically, areas of high correlation adjacent to areas of low correlation may indicate that areas having a low correlation value include abnormal cardiac substrate. Ablation therapy may be targeted at such areas of low correlation including the boundary between spatially adjacent areas of low and high correlation, e.g., the border zone of an infarct which is a common target for therapeutic ablation of myocardial infarction patients with re-entrant ventricular arrhythmias. A visual representation of correlation map 76 may be displayed on display 60.

The boundary between an area of high correlation and an area of low correlation delineates the border-zone of the infarct, separating the infarct from the healthy tissue. During a re-entrant arrhythmia, such infarcts usually include a rotor around the re-entry point. The rotor is identified by determining the area/region which is electrically most incongruous with the rest of the other areas. The rotor-boundary may either form an anatomic block or a functional block. In complex arrhythmias, like an AF, the rotor may also precess or form a trajectory of its own over different cycles.

As such, an area of cardiac tissue associated with an average correlation coefficient having a low value may indicate that a rotor or a myocardial scar exists in that low correlation area. Specifically, the boundary between regions of high correlation and low correlation may be indicative of abnormal substrate. Abnormal substrate may be a potential target for ablation, as ablation disrupts the abnormal conduction paths, which may prevent re-entrant arrhythmias.

Exemplary correlation map 76 shows a couple of areas of interest. Correlation map 76 shows exemplary area I 80, area II 82, area III 84, area IV 86, area V 88, area VI 90, area VII 92, area VIII 94, area IX 96, area XI 97, selected area 98, area XII 99, selected area 100, area XIV 101, area X 102 and area XIII 103. In the exemplary correlation map 76, the average correlation coefficient associated with area I 80 has a value of 0.95 or above. The average correlation coefficient associated with area II 82 has a value of 0.9 or above, but below 0.95. The average correlation coefficient associated with area III 84 and area IV 86 has a value of 0.85 or above, but below 0.9. The average correlation coefficient associated with area V 88 has a value of 0.8 or above, but below 0.85. The average correlation coefficient associated with area VI 90 has a value of 0.75 or above, but below 0.8. The average correlation coefficient associated with area VII 92 has a value of 0.7 or above, but below 0.75. The average correlation coefficient associated with area VIII 94 and area IX 96 has a value that is below 0.7.

The average correlation coefficient associated with area XI 97 has a value of 0.7 or above, but below 0.75. The average correlation coefficient associated with area XII 99 has a value of 0.8 or above, but below 0.85. The average correlation coefficient associated with area XIV 101 has a value of 0.75 or above, but below 0.8. The average correlation coefficient associated with area XIII 103 has a value of 0.7 or above, but below 0.75.

As such, correlation map 76 indicates that area I 80, area II 82, area III 84, area IV 86 and area V 88 are areas of healthy cardiac tissue, as the electrogram signals from these areas are highly correlated with the electrogram signals from neighboring areas. Correlation map 76 also indicates that areas VI 90, area VII 92, area VIII 94, area XIII 103, area XI 97 and area IX 96 are areas of low correlation, i.e., the electrogram signals from these areas and the electrogram signals from neighboring areas have a low correlation. Specially, correlation map 76 indicates that area VII 92, area VIII 94, area IX 96, area XI 97, and area XIII 103 are the areas that have the lowest correlation. The electrogram signals recorded at these areas of low correlation are poorly correlated with the electrogram signals recorded at areas of high correlation.

Since the areas of low correlation may be indicative of abnormal substrate, these areas may be selected for ablation. A border around the areas of low correlation may be drawn to delineate selected area A 98 and selected area 100. Selected area A 98 includes area IX 96, which has a low correlation coefficient with a value below 0.7, area XI 97, which has a low correlation coefficient with a value of 0.7 or above, but below 0.75, and area XII 99, which has a correlation coefficient with a value of 0.8 or above, but less than 0.85.

Selected area B 100 includes area 90 VI, which has a correlation value of 0.75 or above, but below 0.8; area VII 92 which has a correlation value of 0.7 or above but less than 0.75; area VIII 94, which has a correlation value below 0.7, area XIV 101 which has a correlation coefficient value of 0.75 or above, but below 0.8, and area XIII 103, which has a correlation coefficient value of 0.7 or above, but below 0.75.

The boundaries of selected area A 98 and selected area B 100 may, for example, identify a myocardial scar boundary. As such, selected area A 98 and area B 100 may be selected for ablation. The cardiac tissue inside the borders of selected area A 98 and selected area B 100 may be ablated. If so, area X 102 will be an island of surviving cardiac tissue after the ablation of selected area A 98 and selected area B 100.

In another exemplary embodiment, the boundaries of the areas can be defined according to a particular specified gradient. For example, if the difference in the correlation value is 0.2, then the mapping may be configured to visually depict this difference. The size of an area selected for ablation may be customized depending on the differences of the correlation value associated with the area and the correlation values associated with neighboring areas.

Figure 9:
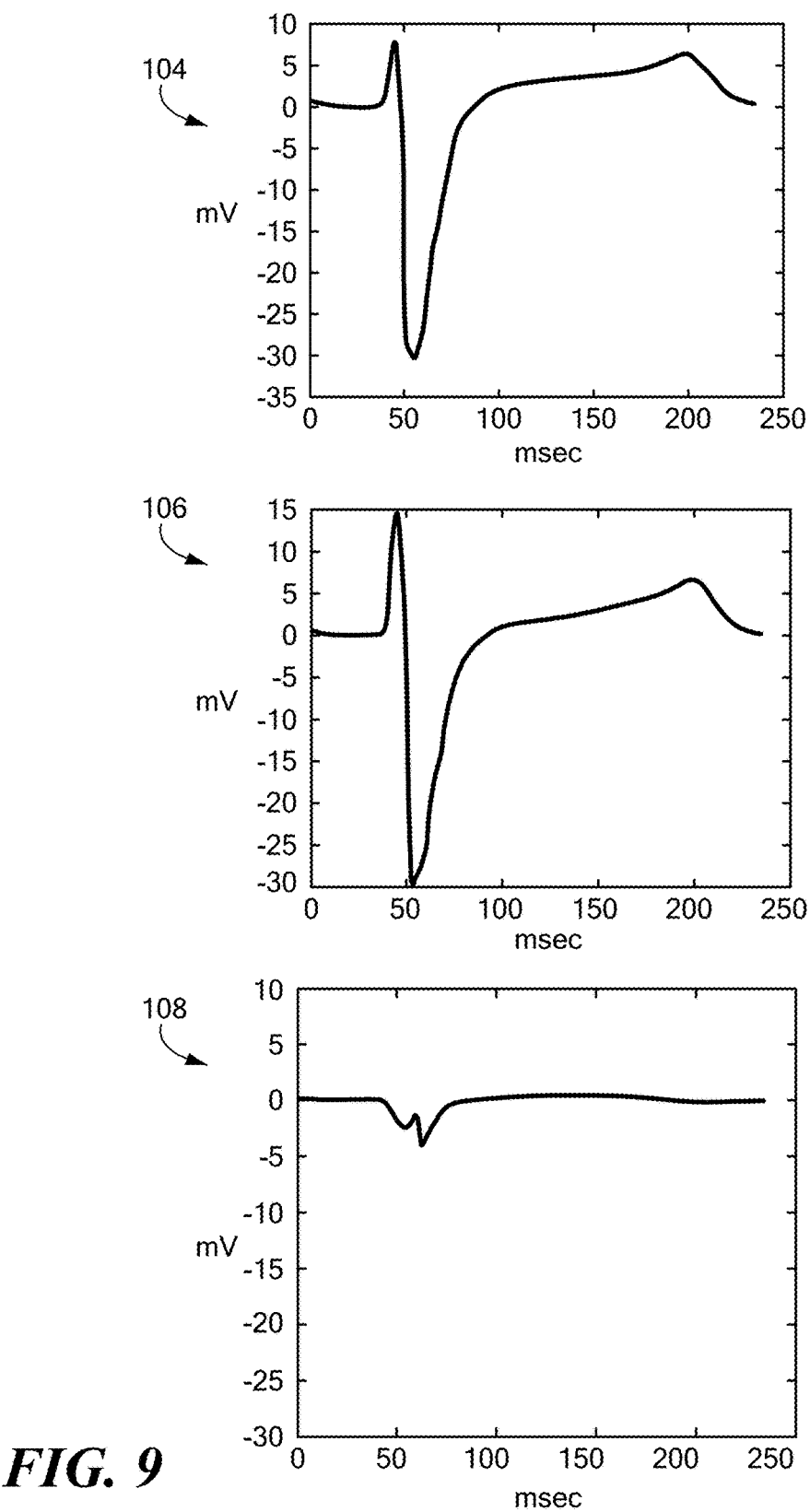
FIG. 9 is an illustration of three different electrogram signals in accordance with the principles of the present invention.

FIG. 9 illustrates the graphs of three different electrogram signals 104, 106 and 108. The graphs illustrate how the voltage of the electrogram signals 104, 106 and 108 changes as a function of time (milliseconds). Electrogram signal 104 and electrogram signal 106 are highly correlated, i.e., changes in the voltage (millivolts) of electrogram signal 104 as a function of time mimic the changes in voltage of electrogram signal 106 as a function of time. Electrogram signal 104 and electrogram signal 106 may correspond to, for example, area III 84 and area IV 86 of FIG. 8 respectively. Electrogram signals 104 and 106 may correspond to two neighboring electrodes 34, such as electrode e3 34*d* and electrode e5 34*f*.

Electrogram signal 108 may correspond to, for example, electrode 34*a* positioned in a border zone area neighboring the two electrodes 34 (e.g., electrode e3 34*d* and electrode e5 34*f*), such as area VII 92 (shown in FIG. 8). The electrogram signal 108 is poorly correlated with both electrogram signals 104 and 106. The low correlation may indicate that area VII 92 may include abnormal cardiac substrate, which may be the target of ablation for, for example, re-entrant arrhythmias.

Figure 10:
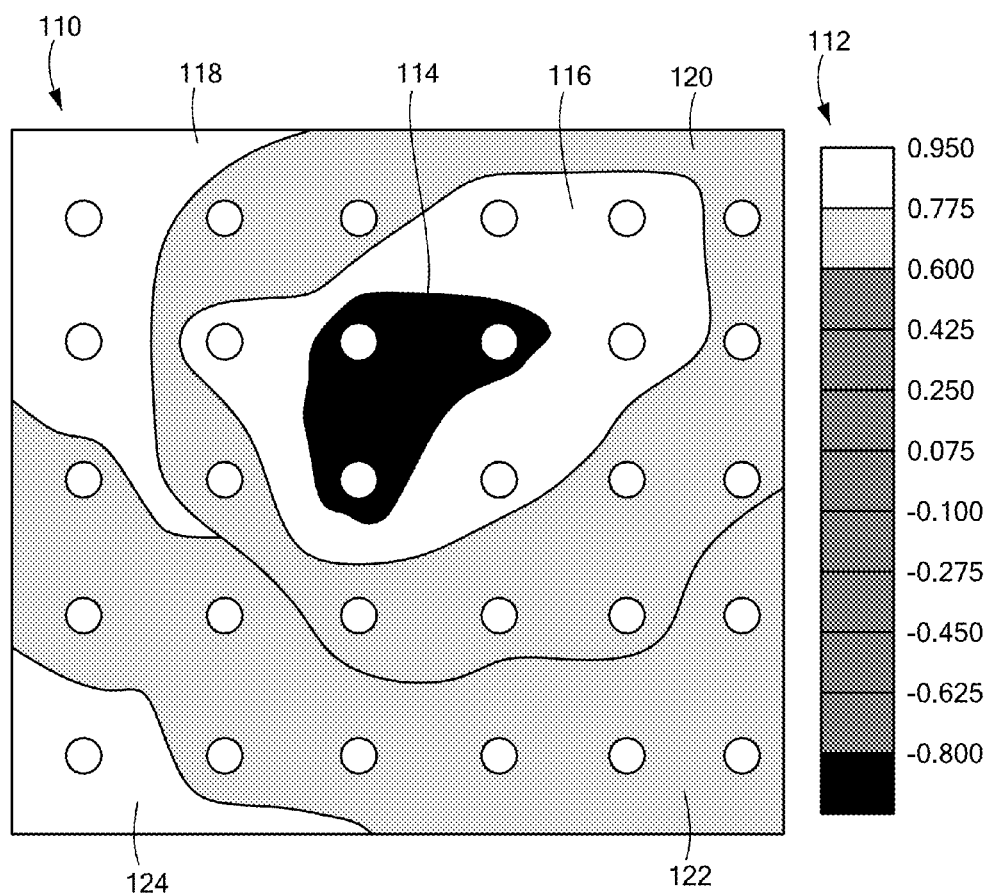
FIG. 10 is a graph of still another exemplary correlation map created using both positive and negative correlation coefficients constructed in accordance with the principles of the present invention.

FIG. 10 shows another exemplary correlation map 110 and a color key 112. Exemplary correlation map 110 was produced using correlation coefficients having values that range from positive to negative. For example, area I 114 has a low average correlation coefficient that is below −0.8. The rest of the areas in correlation map 110, e.g., area II 116, area III 118, area IV 120, area V 122 and area V 124, have an average correlation coefficient above 0.6. Exemplary correlation map 110 may indicate that area I 114 is a possible candidate for ablation, as it may include a myocardial scar, a discontinuation in conduction, etc.

Of note, while the disclosure refers to cardiac tissue, the invention is not limited to such, as any type of tissue may be mapped using the methods described herein. Further, while the disclosure refers to correlation as an exemplary method of comparing electrogram signals, any method of comparing signals may be used. Further, the methods described may be applied epicardially, endocardially or in any area of the body.

Figure 11:
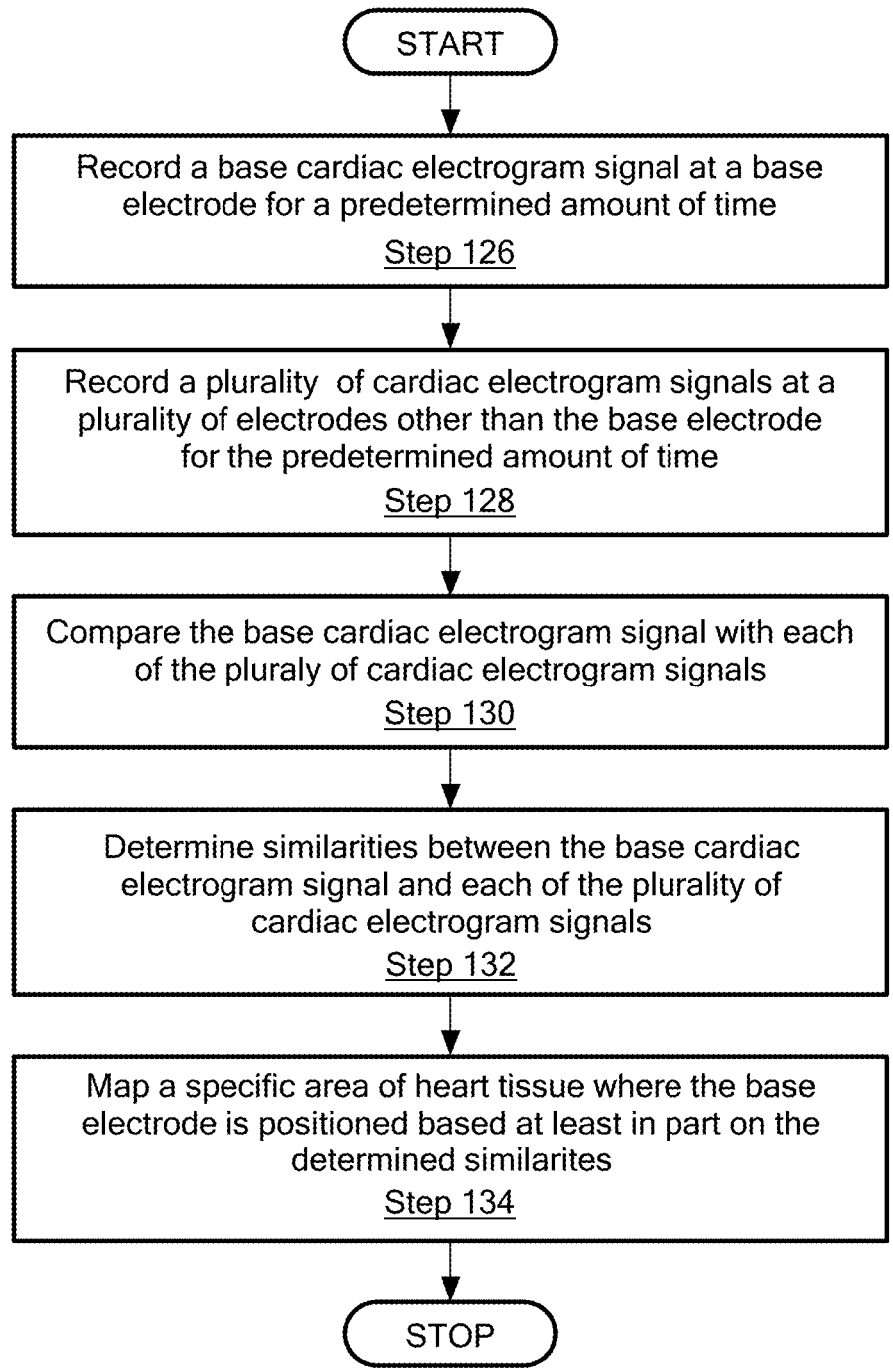
FIG. 11 is a flow chart illustrating an exemplary method of cardiac substrate mapping using spatial correlation maps between neighboring unipolar electrograms.

Referring now to FIG. 11, a flow chart illustrating the various steps of an exemplary method for mapping cardiac tissue is depicted. The method includes providing the medical device 12 having the plurality of electrodes 34 coupled to the distal portion 20. The plurality of electrodes 34 may be positioned proximate and/or in direct contact with a tissue region to be examined, for example, the myocardium or any cardiac tissue. When positioned proximate or in contact with the target tissue region, radiofrequency energy may be transmitted between the plurality of electrodes 34 and/or from at least one of the plurality of electrodes 34 to the reference electrode.

In step 126, a base cardiac electrogram signal may be recorded at a base electrode (Step 126). The base cardiac electrogram signal may be recorded for a predetermined length of time. In one exemplary embodiment, the signal recorded may be an electrocardiogram signal (ECG) recorded proximate the myocardium. The recorded signal may be in vivo or may be a previously recorded signal.

In step 128, a plurality of cardiac electrogram signals at a plurality of electrodes other than the base electrode are recorded for the predetermined amount of time (Step 128). The base cardiac electrogram signal is compared to each of the plurality of cardiac electrogram signals in order to determine how the base cardiac electrogram signal is similar or different to each of the other cardiac electrogram signals (Step 130). The similarities or differences between the base cardiac electrogram signal and each of the plurality of cardiac electrogram signals is determined (Step 132). A specific area of cardiac tissue where the base electrode is positioned is mapped based at least in part on the determined similarities or differences (Step 134).

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of treating arrhythmogenic cardiac tissue, comprising:
    recording a base cardiac electrogram signal at a base electrode for a predetermined amount of time;
    recording a plurality of cardiac electrogram signals at a plurality of electrodes other than the base electrode for the predetermined amount of time;
    comparing the base cardiac electrogram signal with each of the plurality of cardiac electrogram signals;
    determining an average correlation coefficient associated with the base cardiac electrogram signal and each of the plurality of cardiac electrogram signals;
    mapping a specific area of cardiac tissue where the base electrode is positioned based at least in part on the determined average correlation coefficient;
    analyzing the average correlation coefficient to determine whether the average correlation coefficient has a low value;
    identifying the specific area of cardiac tissue as arrhythmogenic cardiac tissue when the average correlation coefficient has a low value;
    providing a medical device including an ablation element;
    identifying a closed boundary between the arrhythmogenic cardiac tissue and surrounding cardiac tissue based at least in part on the average correlation coefficient;
    placing the medical device in contact with the arrhythmogenic cardiac tissue; and
    activating the ablation element and ablating substantially all of the arrhythmogenic cardiac tissue within the boundary.

2. The method of claim 1, wherein the average correlation coefficient is determined using a plurality of correlation coefficients.

3. The method of claim 2, wherein each of the plurality of correlation coefficients is a Pearson correlation coefficient, and wherein each of the plurality of correlation coefficients is computed using the formula:

$$r = \frac{\sum_{i=1}^{n}(X_i - \overline{X})(Y_i - \overline{Y})}{\sqrt{\sum_{i=1}^{n}(X_i - \overline{X})^2}\sqrt{\sum_{i=1}^{n}(Y_i - \overline{Y})^2}}$$

wherein X represents a sample value of the base cardiac electrogram signal at a time, Y represents a sample value of one of the plurality of cardiac electrogram signals at the time, and n is a number of sample values obtained from the base cardiac electrogram signal.

4. The method of claim 1, wherein the base electrode is included on the medical device, the method further comprising providing a reference electrode a distance from the medical device and transmitting energy from the base electrode to the reference electrode.

5. The method of claim 1, further comprising displaying an image corresponding to the specific area of cardiac tissue, wherein the image includes a visual representation of an average of the determined similarities between the base cardiac electrogram signal and each of the plurality of cardiac electrogram signals.

6. The method of claim 1, wherein the recording of the base cardiac electrogram signal and the recording of the plurality of cardiac electrogram signals occur substantially simultaneously.

7. The method of claim 1, wherein the predetermined distance is between one millimeter and twenty millimeters.

8. The method of claim 1, further comprising:
    measuring a cycle length of an arrhythmia in a patient having atrial fibrillation,
    the predetermined amount of time being substantially equal to the cycle length of the arrhythmia.

9. A medical system, comprising:
    a medical device including a base electrode and a plurality of electrodes; and
    a control unit in communication with the base electrode and the plurality of electrodes, the control unit operable to:
        record a base cardiac electrogram signal at a base electrode for a predetermined amount of time;
        record a plurality of cardiac electrogram signals at a plurality of electrodes other than the base electrode for the predetermined amount of time;
        compare the base cardiac electrogram signal with each of the plurality of cardiac electrogram signals;
        determine an average correlation coefficient associated with the base cardiac electrogram signal and each of the plurality of cardiac electrogram signals;
        map a specific area of cardiac tissue where the base electrode is positioned based at least in part on the determined average correlation coefficient;
        analyze the average correlation coefficient to determine whether the average correlation coefficient has a low value;
        identify the specific area of cardiac tissue as arrhythmogenic cardiac tissue when the average correlation coefficient has a low value;
        identify a closed boundary between the arrhythmogenic cardiac tissue and surrounding cardiac tissue based at least in part on the average correlation coefficient;
        place the medical device in contact with the arrhythmogenic cardiac tissue; and
        activate the plurality of electrodes and ablating substantially all of the arrhythmogenic cardiac tissue within the boundary.

10. The medical system of claim 9, further comprising a display, the control unit being further operable to display an image corresponding to the specific area of cardiac tissue on the display, wherein the image includes a visual representation of an average of the determined average correlation coefficients between the base cardiac electrogram signal and each of the plurality of cardiac electrogram signals.

11. The medical system of claim 9, wherein the control unit is further operable to:
    determine whether the mapping of the specific area of cardiac tissue is similar to a mapping of a neighbor area of cardiac tissue; and
    if it is determined that the mapping of the specific area of cardiac tissue is not similar to the mapping of the neighbor area of cardiac tissue, then determining that one of the specific area of cardiac tissue and the neighbor area of cardiac tissue includes one of damaged and arrhythmogenic cardiac tissue.

12. The medical system of claim 9, wherein each of the plurality of electrodes has a neighbor electrode positioned at a neighbor area of cardiac tissue, the control unit being further operable to:

record a neighbor cardiac electrogram signal at the neighbor electrode for the predetermined amount of time;
compare the neighbor cardiac electrogram signal with the base cardiac electrogram signal;
compare the neighbor cardiac electrogram signal with each of the plurality of cardiac electrogram signals other than the neighbor cardiac electrogram signal;
determine similarities between:
  the neighbor cardiac electrogram signal and the base cardiac electrogram signal; and
  the neighbor cardiac electrogram signal and each of the plurality of cardiac electrogram signals other than the neighbor cardiac electrogram signal; and
map the neighbor area of cardiac tissue based at least in part on the determined similarities.

13. The medical system of claim 12, wherein the control unit is further operable to:
  determine a plurality of neighbor correlation coefficients, wherein each of the plurality of neighbor correlation coefficients corresponds to the neighbor electrogram signal and one of a different one of the plurality of cardiac electrogram signals and the base cardiac electrogram signal;
  average the plurality of neighbor correlation coefficients; and
  associate an average of the plurality of neighbor correlation coefficients to the neighbor area of cardiac tissue where the neighbor electrode is positioned.

14. The medical system of claim 13, further comprising a display, the control unit being further operable to:
  display an image on the display, the image being associated with the specific area of cardiac tissue and the neighbor area of cardiac tissue, wherein the image includes a visual representation of:
    an average of the plurality of correlation coefficients; and
    an average of the plurality of neighbor correlation coefficients.

15. The medical system of claim 13, wherein the control unit is further operable to:
  determine whether the average of the plurality of correlation coefficients is different than the average of the plurality of neighbor correlation coefficients; and
  if it is determined that the average of the plurality of correlation coefficients is different than the average of the plurality of neighbor correlation coefficients, then determining that one of the specific area of cardiac tissue and the neighbor area of cardiac tissue includes one of damaged and arrhythmogenic cardiac tissue.

* * * * *